United States Patent [19]

Stephan et al.

[11] Patent Number: 4,965,068

[45] Date of Patent: Oct. 23, 1990

[54] POLYVALENT HYPERIMMUNOGLOBULIN PREPARATION

[75] Inventors: Wolfgang Stephan, Dreieich; Herbert Dichtelmuller, Sulzbach; Michael Kloft, Darmstadt, all of Fed. Rep. of Germany

[73] Assignee: Biotest Pharma GmbH, Frankfurt, Fed. Rep. of Germany

[21] Appl. No.: 370,118

[22] Filed: Jun. 23, 1989

Related U.S. Application Data

[63] Continuation of Ser. No. 124,334, Nov. 19, 1987, abandoned, which is a continuation of Ser. No. 859,840, May 5, 1986, abandoned.

[30] Foreign Application Priority Data

May 4, 1985 [DE] Fed. Rep. of Germany ....... 3516119

[51] Int. Cl.$^5$ ............................................. A61K 39/40
[52] U.S. Cl. ..................................... 424/87; 424/85.8; 424/86; 530/387
[58] Field of Search .................... 424/85.8, 86, 87; 530/387

[56] References Cited

U.S. PATENT DOCUMENTS

| | | | |
|---|---|---|---|
| 4,029,762 | 6/1977 | Galanos et al. | 424/87 |
| 4,174,388 | 11/1979 | McAleer et al. | 424/86 |
| 4,428,931 | 1/1984 | Tolman et al. | 424/87 |
| 4,587,121 | 5/1986 | Collins et al. | 424/87 |

FOREIGN PATENT DOCUMENTS 0014333  1/1980  Fed. Rep. of Germany .

OTHER PUBLICATIONS

Teng et al., Proc. Natl. Acad. Sci., USA 82, 1790-1794, (1985).
New England Journal of Medicine, 307 (1982), pp. 1225-1230, Braude et al.

*Primary Examiner*—Howard E. Schain
*Attorney, Agent, or Firm*—Wegner & Bretschneider

[57] ABSTRACT

The present invention involves a polyvalent hyperimmunoglobulin preparation having activity against gram negative and gram positive bacteria. Such a polyvalent hyperimmunoglobulin preparation is prepared from plasma, serum or whole blood from donors. Donor selection is based upon titer against *E. coli* J5 antigen or against lipid A antigen.

21 Claims, No Drawings

POLYVALENT HYPERIMMUNOGLOBULIN PREPARATION

This application is a continuation of Ser. No. 124,334, filed Nov. 19, 1987, which is a continuation of Ser. No. 859,840, filed May 5, 1986, both now abandoned.

This invention relates to a new polyvalent hyperimmunoglobulin preparation and a process for obtaining this polyvalent hyperimmunoglobulin preparation.

The serological differences between bacteria are determined by surface-bound, species-specific antigens. Thus, specific antibodies, e.g., against Salmonella, will not bind at all or only very weakly to antigens of other bacteria, e.g., Pseudomonas. Therefore, therapy and prophylaxis of bacterial infections requires a unique hyperimmunoglobulin or hyperimmunoserum for each individual pathogen. This substantially restricts the useful application of hyperimmunoglobulins.

On the other hand, it is known that the group of the gram-negative bacteria (Salmonella, E. coli, Serratia, Pseudomonas and others) have a common antigen. Immunoserum directed against this antigen was obtained by Braude and Ziegler (Ziegler et al., The New England Journal of Medicine 307, 1982, pp. 1225 to 1230) and used successfully in human patients having gram-negative infections. This hyperimmunoserum was obtained by immunizing healthy donors with a vaccine of the E. coli mutant J5. Thus, is is known that an immunoserum active against the antigen common to the gram-negative bacteria can be obtained by vaccination of donors with a vaccine of the E. coli mutant J5.

One object of the present invention is to obtain an immunoglobulin preparation which has activities against gram-negative organisms and which can be obtained without the need to immunize human donors.

Another object of this invention is an immunoglobulin preparation which also exhibits activities against gram-positive organisms.

These objectives are attained with the present invention.

We have discovered that even in normal populations of unvaccinated persons, activities against the antigen common to the group of the gram-negative organisms are found. Thus, antibodies against E. coli J5 antigen occur naturally, and individuals with high antibody titers against E. coli J5 antigen can be distinguished. It was also discovered that individuals having high activities against E. coli J5 show clear increases in antibody activities against other gram-negative organisms. This is not the case in a population having low titers against E. coli J5; here (FIG. 1) only one individual out of 10 exhibits increased titers against other gram-negative pathogens. Surprisingly however, besides the titers against gram-negative bacteria, the titers against gram-positive bacteria are also markedly increased. This is all the more astonishing, given that gram-positive bacteria differ from gram-negative bacteria as a result of fundamentally different wall structure.

Whereas a high plasma antibody titer against E. coli J5 correlates with a high titer against other bacteria, a high titer (1:320) against Pseudomonas may be associated with a low titer against E. coli J5 (1:20) or against Staphylococcus (<10). It was found that a plasma sample can exhibit a titer of 1:160 against E. coli and simultaneously exhibit a titer of <10 against staphylococci and streptococci. From this it follows that screening of plasma for high titers against E. coli J5 leads to a selection of plasmas which exhibit high antibody titers against both gram-negative and gram-positive germs, whereas a screening of plasma for high antibody titers against other antigens will not provide this result.

By means of a screening among plasmapheresis donors having an elevated titer against E. coli J5, it is thus also possible to find donors who show elevated titers against other gram-negative organisms and against gram-positive bacteria a well.

In the group of gram-negative bacteria is found another common antigen, lipid A, which is the lipid moiety of the lipopolysaccharide cell wall. Lipid A is thus part of the highly antigenic structure of these gram-negative organisms. Lipid A is also responsible for toxic reactions (pyrogenicity). By means of a screening among plasmapheresis donors having an elevated titer against lipid A, in the same manner described above in connection with the E. coli J5 antigen, we have unexpectedly also been able to determine donors having elevated titers against other gram-negative and gram-positive bacteria. Elevated titers against E. coli J5 are typically titers corresponding to a value of at least 1:160 in the passive hemaglutination test. Titers of 1:320 and higher are especially preferred.

Titers against lipid A are desirably at least 20, but preferably at least 40 times higher than in the average donor population.

If one prepares an immunoglobulin preparation from the plasma of such donors with high titers against J5 antigen or lipid A, e.g., by known processes via the II/III or II Cohn fraction, the result is a preparation which is characterized by high titers against gram-negative and gram-positive organisms. Table 1 shows these titers in comparison with a conventional immunoglobulin preparation.

Upon investigation of the immunoglobulin preparation obtained in this manner, we discovered that, in addition to IgG as the main constituent, they also contain substantial amounts of antibodies of the IgA and IgM classes. In general, IgG and IgA are 7s molecules; in general, IgM is a 19s molecule (see Lexikon Biochemie, Leipzig, 1976, p. 509). The fragments of the above-cited molecules, obtained in a known manner, may also be incorporated into preparations of the invention.

In this manner, one obtains an immunoglobulin preparation which can be used against a broad spectrum of bacterial infections, also mixed infections, and simultaneously has activities which correspond to special hyperimmunoglobulins against various types of organisms, and thus represents a polyvalent hyperimmunoglobulin preparation.

EXAMPLE 1:

Donor plasma was screened for high titers against E. coli J5 by means of the passive hemaglutination test. For this purpose, the supernatant of an autoclaved overnight culture of E. coli J5 (ATCC 39041) was used as antigen.

Plasmas having reciprocal titers of 1:320 and higher were selected and combined. 4240 ml of this plasma pool were fractionated according to Cohn, the II/III fraction being processed by means of octanoic acid and calcium phosphate. 207 ml of a 5% immunoglobulin solution was obtained and was modified for intravenous application by means of beta-propiolactone. After intensive diafiltration and subsequent sterile filtration, about 180 ml of end product was obtained.

The preparation contains 4160 mg/100 ml IgG, measured by means of Kallestad Quantiplate, 480 mg/100 ml IgA and 960 mg/100 ml IgM. The determination of the antibody titers in the passive hemagglutination yielded the values shown in Table 1.

EXAMPLE 2:

Using the process corresponding to Example 1, 200 ml of IgM-enriched immunoglobulin solution, for intravenous application, was obtained from 4290 ml of screened plasma.

EXAMPLE 3:

50 ml of an IgM-enriched immunoglobulin solution (5%) was obtained from 4.35 liters of screened plasma in accordance with Example 1, by use of the Cohn fraction III. The antibody titer against lipid A was approximately 20 to 38 times higher in this preparation than that which would be found in a serum pool from unscreened blood donors.

EXAMPLE 4:

1.4 Liters of a stabilized stored serum was prepared from 2.4 liters of screened plasma by treatment with beta-propiolactone, UV and Aerosil according to the process described in European patent application A-14 333. Here too, the antibody titers against lipid A were approximately 20 to 40 times higher than in a plasma from unscreened blood donors. The antibody titers of this preparation against various other antigens are shown in Table 2.

TESTING BY ANIMAL EXPERIMENTS

To determine the effectiveness of the polyvalent hyperimmunoglobulin prepared from the screened plasma, 0.5 ml of a 5% solution was administered intravenously to mice, which then were infected intraperitoneally with $10^7$ CFU (colony-forming units) of *Pseudomonas aeruginosa* per animal. Serving as comparison was a group of animals which received immunoglobulin from unscreened plasma. In the control group, the infected animals remained untreated. Each group comprised 21 animals. 25 hours after infection, only 14.3% of the animals in the untreated control group survived. 47.6% of the animals (10 out of 21) were protected by immunoglobulin from unscreened plasma; in the group of the animals treated with immunoglobulin 71.4% (15 out of 21 animals) were protected (Table 3). Hence, nearly twice as many animals died from infection-related causes in the group treated with immunoglobulin from unscreened plasma as in the group treated with immunoglobulin from screened plasma. Thus, the screened plasma preparation exhibits a considerably increased effectiveness.

TABLE 1

Reciprocal antibody titers (PHA) against gram-negative and gram-positive germs.
Comparison of three immunoglobulin solutions.

| Antigen | Reciprocal titer PHA | | |
|---|---|---|---|
| | Preparation 1 | Preparation 2 | Preparation 3 |
| E. coli J5 | 320 (40) | 1280 | 2560 |
| E. coli | 1280 | 1280 | 5120 |
| Ps. aerug. | 1280 | 10240 | 5120 |
| Klebs. pneu. | 640 | 2560 | 640 |
| Staph. aur. | 80 | 640 | 320 |
| Enterococc. | 80 | 640 | 320 |
| Str. pyog. | 160 | 320 | 160 |
| Str. virid. | 160 | 160 | 320 |

TABLE 1-continued

Reciprocal antibody titers (PHA) against gram-negative and gram-positive germs.
Comparison of three immunoglobulin solutions.

| Antigen | Reciprocal titer PHA | | |
|---|---|---|---|
| | Preparation 1 | Preparation 2 | Preparation 3 |
| Pneumoc. | n.d. | n.d. | 80 |

Preparation 1: IgM-enriched immunoglobulin solution from unscreened plasma
Preparations 2 and 3: IgM-enriched immunoglobulin solution prepared from *E. coli* J5-screened plasma

TABLE 2

Reciprocal titers against bacterial antigens in stored serums

| Preparation | Antigen | | | |
|---|---|---|---|---|
| | E. coli | Ps. aerug. | Klebs. pneum. | Staph. aureus |
| Stored serum from screened plasma | 320 | 1280 | 320 | 160 |
| Stored serum from unscreened plasma | 80 | 80 | 40 | 40 |

TABLE 3

Effectiveness of immunoglobulin solutions against *Pseudomonas aeruginosa* infection Survival of *Pseudomonas aeruginosa*-infected mice 24 h after infection

| Treatment | $N_s/N_0$ | % | $N_d/N_0$ |
|---|---|---|---|
| Untreated controls | 3/21 | 14.3 | 18/21 |
| Immunoglobulin from unscreened plasma | 10/21 | 47.6 | 11/21 |
| Immunoglobulin from *E. coli* J5-screened plasma | 15/21 | 71.6 | 6/21 |

$N_s$ = number of surviving animals
$N_d$ = number of dead animals
$N_0$ = total number at beginning of test

What is claimed is:

1. A process for making a human polyvalent hyperimmunoglobulin preparation having activities against gram-negative as well as against gram-positive bacteria and comprising the steps of:
   (a) screening plasma, serum or whole blood from human donors for a titer of antibody to *E. coli* J5 antigen of at least 1:160 by means of passive hemagglutination test,
   (b) pooling the donor plasma, serum or whole blood according to step (a) above, and
   (c) preparing an immunoglobulin fraction from the plasma serum or blood pooled according to step (b) by means of the Cohn fractionation method.

2. A process of claim 1, characterized in that after step (c) the reciprocal antibody titer against *E. coli* is at least 1:1280.

3. A process of claim 1, characterized in that after step (c) the reciprocal antibody titer against *Ps. aeruginosa* is at least 1:1280.

4. A process according to claim 1, wherein the preparation contains the main constituent IgG, and also containing IgA and IgM antibodies, and wherein IgG and IgM are present as 7s and 19s molecules or fragments thereof.

5. A human polyvalent hyperimmunoglobulin preparation having activities against gram-negative as well as against gram-positive bacteria and produced by a process comprising the steps of:
   (a) screening plasma, serum or whole blood from human donors for a titer of antibody to *E. coli* J5 antigen of at least 1:160 by means of passive hemagglutination test, (b) pooling the donor plasma, serum or whole blood according to step (a) above, (c) preparing an immunoglobulin fraction from the plasma serum or blood pooled according to step (b) by means of the Cohn fractionation method.

6. A preparation of claim 5, characterized in that after step (c) the reciprocal antibody titer against *E. coli* is at least 1:1280.

7. A preparation of claim 5, characterized in that after step (c) the reciprocal antibody titer against *Ps. aeruginosa* is at least 1:1280.

8. A preparation according to claim 5, containing the main constituent IgG, and also containing IgA. and IgM antibodies, wherein IgG and IgM are present as 7s and 19s molecules or fragments thereof.

9. A process for treating an animal having a gram-positive bacterial infection comprising administering to said animal an effective amount of the preparation of claim 5.

10. A process for treating an animal having a gram-negative bacterial infection comprising administering to said animal an effective amount of the preparation of claim 5.

11. A process for treating an animal having a *Staphyloccus aureaus* bacterial infection comprising administering to said animal an effective amount of the preparation of claim 5.

12. A process for treating an animal having an Enterococcus bacterial infection comprising administering to said animal an effective amount of the preparation of claim 5.

13. A process for treating an animal having a *Streptococcus pyogenes* bacterial infection comprising administering to said animal an effective amount of the preparation of claim 5.

14. A process for treating an animal having a *Streptococcus viridans* bacterial infection comprising administering to said animal an effective amount of the preparation of claim 5.

15. A process of claim 1, characterized in that after step (c) the reciprocal antibody titer against *Staph. aureus* is at least 1:320 and against Enterococcus is at least 1:320.

16. A preparation of claim 5, characterized in that after step (c) the reciprocal antibody titer against *Staph. aureus* is at least 1:320 and against Enterococcus is at least 1:320.

17. A human polyvalent hyperimmunoglobulin preparation suitable for intravenous application active against gram-negative as well as gram-positive bacteria, wherein the reciprocal antibody titer against *E. coli* J5 is at least 1:1280, against Staph. aureus at least 1:320 and against Enterococcus at least 1:320.

18. A preparation according to claim 17 comprising IgG, IgA, and IgM antibodies, wherein IgG and IgM are present as 7S and 19S molecules or fragments thereof.

19. A human polyvalent hyperimmunoglobulin preparation suitable for intravenous application against gram-negative as well as gram-positive bacteria prepared from pooled plasma, serum, or whole blood from human donors having a reciprocal antibody titer against *E. coli* J5 antigen of at least 1:160.

20. A preparation according to claim 19, wherein the reciprocal antibody titer against *E. coli* J5 in the human donors is at least 1:320.

21. A preparation according to claim 19, comprising IgG, IgA, and IgM antibodies, wherein IgG and IgM are present as 7S and 9S molecules or fragments thereof.

* * * * *